United States Patent
Boutoussov et al.

(10) Patent No.: US 12,016,803 B2
(45) Date of Patent: *Jun. 25, 2024

(54) DENTAL LASER UNIT WITH COMMUNICATION LINK TO ASSISTANCE CENTER

(71) Applicant: Biolase, Inc., Foothill Ranch, CA (US)

(72) Inventors: Dmitri Boutoussov, Dana Point, CA (US); David Tuck, Milford, NH (US)

(73) Assignee: Biolase, Inc., Foothill Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/111,279

(22) Filed: Feb. 17, 2023

(65) Prior Publication Data

US 2023/0329954 A1 Oct. 19, 2023

Related U.S. Application Data

(60) Continuation of application No. 17/404,184, filed on Aug. 17, 2021, now Pat. No. 11,583,462, which is a continuation of application No. 16/791,051, filed on Feb. 14, 2020, now abandoned, which is a continuation-in-part of application No. 16/249,829, filed on Jan. 16, 2019, now abandoned, which is a
(Continued)

(51) Int. Cl.
| | |
|---|---|
| *A61G 15/14* | (2006.01) |
| *A61C 1/00* | (2006.01) |
| *A61B 18/00* | (2006.01) |
| *A61B 18/20* | (2006.01) |
| *A61G 15/00* | (2006.01) |

(52) U.S. Cl.
CPC ............ *A61G 15/14* (2013.01); *A61C 1/0015* (2013.01); *A61C 1/0046* (2013.01); *A61B 2018/00791* (2013.01); *A61B 2018/2025* (2013.01); *A61C 2204/005* (2013.01); *A61G 15/00* (2013.01)

(58) Field of Classification Search
CPC ...... A61G 15/14; A61G 15/00; A61C 1/0015; A61C 1/0046; A61C 2204/005; A61B 2018/00791; A61B 2018/2025
USPC .......................................................... 433/29
See application file for complete search history.

(56) References Cited

U.S. PATENT DOCUMENTS

| | | | |
|---|---|---|---|
| 4,761,054 | A | 8/1988 | Ishimori et al. |
| 5,139,494 | A | 8/1992 | Freiberg |

(Continued)

FOREIGN PATENT DOCUMENTS

| | | | |
|---|---|---|---|
| CN | 1246927 | A | 3/2000 |
| CN | 1543368 | A | 11/2004 |

(Continued)

*Primary Examiner* — Mohamed A. Wasel
(74) *Attorney, Agent, or Firm* — Greenberg Traurig, LLP

(57) ABSTRACT

A medical treatment apparatus includes a power and control (PAC) device. The PAC device provides electrical power through a cable to a laser handpiece assembly to electrically power a laser source within the handpiece assembly. The PAC device controls operation of the handpiece assembly and detects an identification of the handpiece assembly. The PAC device also monitors data relating to operation of the handpiece assembly. The PAC device uploads, through a communication network to a user assistance center remote from the PAC device, the handpiece assembly identification and the monitored data.

9 Claims, 4 Drawing Sheets

Related U.S. Application Data division of application No. 14/587,955, filed on Dec. 31, 2014, now abandoned, said application No. 16/791,051 is a continuation of application No. 14/204,773, filed on Mar. 11, 2014, now Pat. No. 10,561,560.

(60) Provisional application No. 61/922,581, filed on Dec. 31, 2013, provisional application No. 61/777,046, filed on Mar. 12, 2013.

(56) References Cited

U.S. PATENT DOCUMENTS

| | | |
|---|---|---|
| 5,741,247 A | 4/1998 | Rizoiu et al. |
| 5,819,229 A | 10/1998 | Boppe |
| 5,825,958 A | 10/1998 | Gollihar et al. |
| 6,026,396 A | 2/2000 | Hall |
| 6,096,025 A | 8/2000 | Borders |
| 6,261,310 B1 | 7/2001 | Neuberger et al. |
| 6,746,473 B2 | 6/2004 | Shanks et al. |
| 6,813,289 B2 | 11/2004 | Gruzdev et al. |
| 7,118,588 B2 | 10/2006 | Tucek et al. |
| 7,298,767 B2 | 11/2007 | Gruzdev et al. |
| 7,548,568 B2 | 6/2009 | Gruzdev et al. |
| 7,702,196 B2 | 4/2010 | Boutoussov et al. |
| 7,922,751 B2 | 4/2011 | Shanks et al. |
| 7,947,067 B2 | 5/2011 | Tucek et al. |
| 8,083,785 B2 | 12/2011 | Shanks et al. |
| 8,439,959 B2 | 5/2013 | Tucek et al. |
| 8,485,818 B2 | 7/2013 | Boutoussov et al. |
| 9,314,374 B2 * | 4/2016 | Artsyukhovich .... A61B 3/0008 |
| 9,433,475 B2 | 9/2016 | Bierbaum et al. |
| 2002/0057203 A1 | 5/2002 | Border et al. |
| 2002/0123781 A1 | 9/2002 | Shanks |
| 2002/0138072 A1 | 9/2002 | Black |
| 2003/0018324 A1 | 1/2003 | Davenport |
| 2003/0021312 A1 | 1/2003 | Gruzdev |
| 2003/0036683 A1 | 2/2003 | Kehr et al. |
| 2004/0006378 A1 | 1/2004 | Shanks |
| 2004/0097910 A1 | 5/2004 | Brugger |
| 2004/0111012 A1 | 6/2004 | Whitman |
| 2004/0158301 A1 | 8/2004 | Tucek |
| 2004/0224279 A1 | 11/2004 | Siemons |
| 2005/0085802 A1 | 4/2005 | Gruzdev |
| 2005/0131499 A1 | 6/2005 | Shanks |
| 2005/0137653 A1 | 6/2005 | Friedman et al. |
| 2005/0170310 A1 | 8/2005 | Schafer |
| 2006/0030891 A1 | 2/2006 | Saltzstein et al. |
| 2006/0064080 A1 | 3/2006 | Cao |
| 2006/0095099 A1 | 5/2006 | Shanks |
| 2006/0206176 A1 | 9/2006 | Shanks |
| 2006/0208931 A1 | 9/2006 | Boese et al. |
| 2006/0224218 A1 | 10/2006 | Tucek |
| 2006/0229690 A1 | 10/2006 | Shanks |
| 2006/0240381 A1 | 10/2006 | Rizoiu et al. |
| 2006/0274794 A1 | 12/2006 | Watanabe et al. |
| 2007/0042315 A1 | 2/2007 | Boutoussov et al. |
| 2007/0135870 A1 | 6/2007 | Shanks |
| 2007/0250137 A1 | 10/2007 | Daffer |
| 2007/0288628 A1 | 12/2007 | Sadovsky et al. |
| 2008/0043790 A1 | 2/2008 | Gruzdev |
| 2008/0097917 A1 | 4/2008 | Dicks et al. |
| 2008/0161783 A1 | 7/2008 | Cao |
| 2008/0281301 A1 | 11/2008 | DeBoer et al. |
| 2009/0030652 A1 | 1/2009 | Greco et al. |
| 2009/0105698 A1 * | 4/2009 | Hodel .................... A61B 18/22 606/11 |
| 2009/0171328 A1 | 7/2009 | Horvath |
| 2009/0204423 A1 | 8/2009 | DeGheest et al. |
| 2009/0257465 A1 | 10/2009 | Gruzdev |
| 2009/0275932 A1 | 11/2009 | Zelickson |
| 2009/0291410 A1 | 11/2009 | Conners |
| 2010/0016931 A1 | 1/2010 | Shanks |
| 2010/0016995 A1 | 1/2010 | Barat |
| 2010/0036535 A1 | 2/2010 | Feine et al. |
| 2010/0167226 A1 * | 7/2010 | Altshuler ............. A61C 1/0015 433/29 |
| 2010/0216088 A1 | 8/2010 | Bierbaum |
| 2010/0235180 A1 * | 9/2010 | Atkinson ............... G01D 15/00 378/207 |
| 2010/0292556 A1 | 11/2010 | Golden |
| 2010/0324380 A1 | 12/2010 | Perkins et al. |
| 2010/0324426 A1 | 12/2010 | Tucek |
| 2011/0030141 A1 | 2/2011 | Soderberg et al. |
| 2011/0039229 A1 | 2/2011 | Senia |
| 2011/0087312 A1 | 4/2011 | Shanks |
| 2011/0144410 A1 | 6/2011 | Kennedy |
| 2011/0179405 A1 | 7/2011 | Dicks et al. |
| 2011/0195374 A1 | 8/2011 | Boren |
| 2011/0208274 A1 | 8/2011 | Bornstein |
| 2011/0225002 A1 | 9/2011 | Fackler et al. |
| 2012/0123399 A1 | 5/2012 | Belikov et al. |
| 2012/0226771 A1 | 9/2012 | Harrington et al. |
| 2013/0036210 A1 | 2/2013 | Birtwhistle |
| 2013/0045456 A1 | 2/2013 | Feine et al. |
| 2013/0104120 A1 | 4/2013 | Arrizza et al. |
| 2013/0176230 A1 | 7/2013 | Georgiev et al. |
| 2013/0221184 A1 | 8/2013 | Odaka et al. |
| 2013/0289548 A1 | 10/2013 | Hamada et al. |
| 2013/0321284 A1 | 12/2013 | Bello et al. |
| 2014/0113243 A1 | 4/2014 | Boutoussov et al. |
| 2014/0128881 A1 | 5/2014 | Tyc et al. |
| 2014/0152466 A1 | 6/2014 | Wiesner et al. |
| 2014/0170588 A1 | 6/2014 | Miller et al. |
| 2014/0363784 A1 | 12/2014 | Monty et al. |
| 2015/0070187 A1 | 3/2015 | Wiesner et al. |
| 2015/0342702 A1 * | 12/2015 | Borgschulte ............. A61C 5/40 433/101 |
| 2015/0342703 A1 | 12/2015 | Monty et al. |
| 2016/0007937 A1 | 1/2016 | Georgiev et al. |
| 2016/0299510 A1 | 10/2016 | Feine et al. |

FOREIGN PATENT DOCUMENTS

| | | |
|---|---|---|
| CN | 1891173 A | 1/2007 |
| CN | 101484082 A | 7/2009 |
| JP | 2012196240 A | 10/2012 |
| WO | 199816855 A1 | 4/1998 |
| WO | 2003017670 A1 | 2/2003 |
| WO | 2006012752 A1 | 2/2006 |
| WO | 2007103158 A2 | 9/2007 |
| WO | 2012074918 A2 | 6/2012 |

* cited by examiner

DENTAL LASER UNIT WITH COMMUNICATION LINK TO ASSISTANCE CENTER

CROSS-REFERENCE TO RELATED APPLICATIONS

This application is a continuation of U.S. application Ser. No. 17/404,184, filed Aug. 17, 2021, entitled "Dental Laser Unit with Communication Link to Assistance Center," which is a continuation of U.S. application Ser. No. 16/791, 051, filed Feb. 14, 2020, entitled "Dental Laser Unit with Communication Link to Assistance Center," which is a continuation of U.S. application Ser. No. 14/204,773, filed Mar. 11, 2014, now U.S. Pat. No. 10,561,560, entitled "Dental Laser Unit with Communication Link to Assistance Center," which claims the benefit of and priority to U.S. Provisional Application No. 61/777,046, filed Mar. 12, 2013, entitled "Permanent Two-Way Access to an Interchangeable Laser Module for a Dental Chair Terminal," and U.S. application Ser. No. 16/791,051 is a continuation-in-part of U.S. application Ser. No. 16/249,829, filed Jan. 16, 2019, entitled "Dual Wavelength Laser Treatment Device," which is a divisional application of U.S. application Ser. No. 14/587,955, filed Dec. 31, 2014, entitled "Dual Wavelength Laser Treatment Device," which claims the benefit of and priority to U.S. Provisional Application No. 61/922,581, filed Dec. 31, 2013, entitled "Dual Wavelength Laser Treatment Device" all of which are incorporated herein by reference.

TECHNICAL FIELD

This relates to medical equipment used by medical professionals to perform medical treatments. It more particularly relates to laser equipment used by dentists to perform laser dental procedures on patients.

BACKGROUND

A laser handpiece, electrically powered by a power supply, is held by a dentist and used to perform dental laser procedures on a patient.

SUMMARY

A medical treatment apparatus includes a power-and-control (PAC) device. The PAC device provides electrical power through a cable to a laser handpiece assembly to electrically power a laser source within the handpiece assembly. The PAC device controls operation of the handpiece assembly and detects an identification of the handpiece assembly. The PAC device also monitors data relating to operation of the handpiece assembly. The PAC device uploads, through a communication network to a user assistance center remote from the PAC device, the handpiece assembly identification and the monitored data.

Preferably, the PAC device downloads an update of software that controls the PAC device, and implements the software update, wherein the update is prepared based on the uploaded data. The PAC device also downloads and implements control instructions that control operation of the PAC device to perform a diagnostic test and upload resulting data to the assistance center. The PAC device also downloads information that is derived from the uploaded data, and displays the information to a user of the apparatus. A dental patient chair assembly, for seating a dental patient undergoing treatment by the handpiece assembly, supports the PAC device.

A hardware server communicates over the network with multiple such PAC devices. The server uploads, from each PAC device through the network, the respective handpiece assembly identification and the monitored data.

Preferably, the server prepares, based on the uploaded data, an update of software that controls the PAC devices, and downloads the update to the PAC devices. The server downloads, to each PAC device, control instructions that control the PAC device to perform a diagnostic test and upload resulting data to the assistance center, and receives the uploaded resulting data from the respective PAC device. The server derives information from the uploaded data, and downloads the information to the PAC devices to be displayed by the PAC devices. The server uploads, from one of the PAC devices, a question regarding use of the handpiece assembly, downloads the question to the other PAC devices, uploads, from the other PAC devices, answers to the question, and downloads the answers to the PAC device from which the question was received. The server uploads, from one of the PAC devices, educational advice on use of the handpiece assembly, and downloads the advice to the other PAC devices. The server is part of an assistance center that is operated by a manufacturer or distributer of the PAC device and the handpiece assembly.

DETAILED DESCRIPTION

Figure 1:
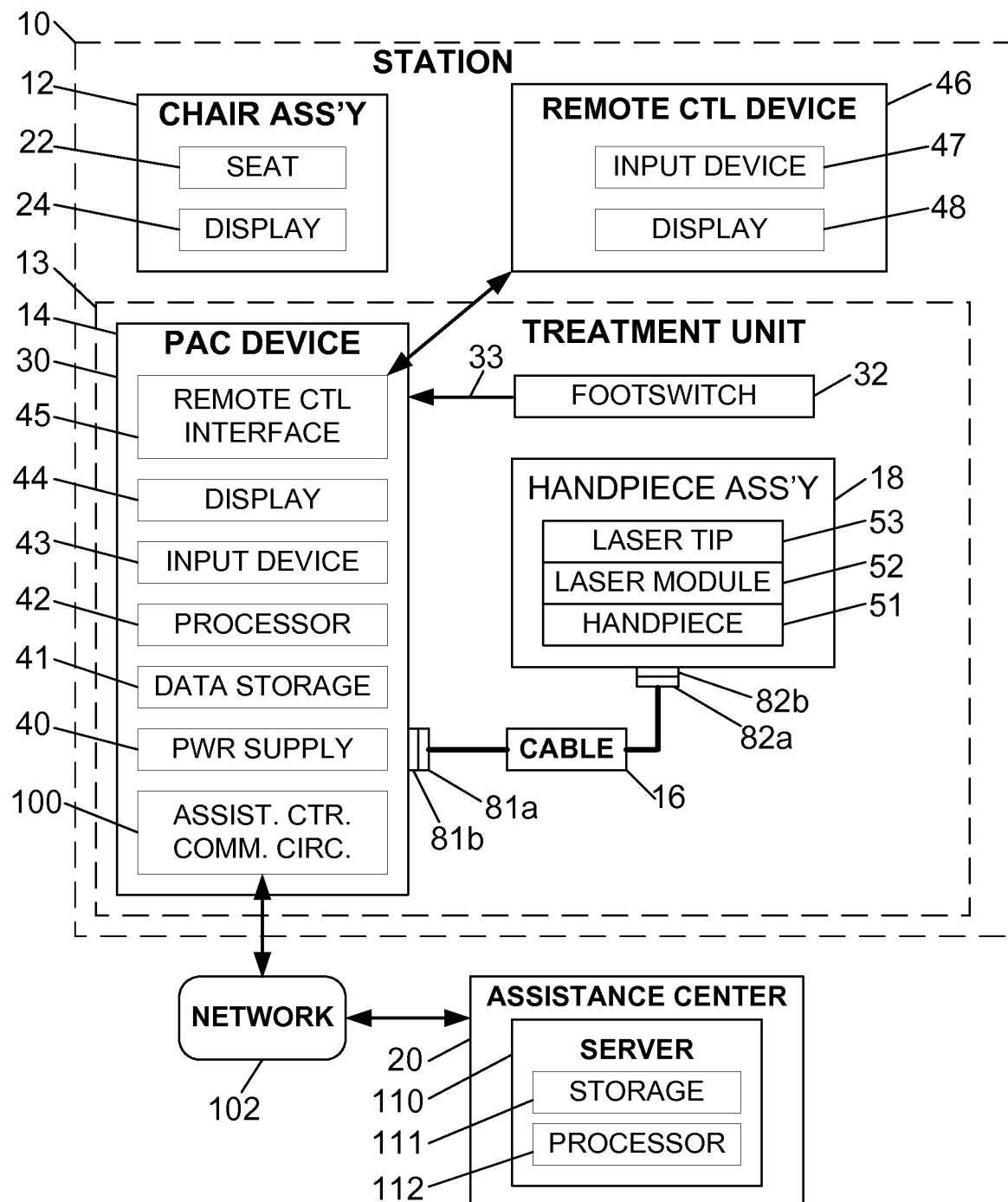
FIG. 1 is a schematic diagram of an example system for performing medical treatment procedures. The system includes a user assistance center in communication with a treatment unit. The treatment unit includes a power-and-control device (PAC device) connected by a cable to a handpiece assembly.

FIG. 1 is a block diagram of an example medical treatment system for use by a medical practitioner for treating a patient. The system includes a medical station apparatus 10 for performing medical treatment procedures. The station apparatus 10 includes a patient chair assembly 12 that the patient sits on and a medical treatment unit 13. The treatment unit 13 includes a power-and-control (PAC) device 14 connected by a cable (hose) 16 to an electrically-powered handheld surgical handpiece assembly 18. The handpiece assembly 18 is held by the practitioner (user) and used to perform a medical procedure on the seated patient. The cable 16 conducts electric power, control signals and coolant from the PAC device 14 to the handpiece assembly and conducts feedback data from the handpiece assembly to the PAC device 14. The PAC device 14 communicates with a remotely located user assistance center 20, to upload data relating to operation of the handpiece assembly 18 and to download software updates, control instructions, and information to be displayed to the practitioner.

Figure 2:
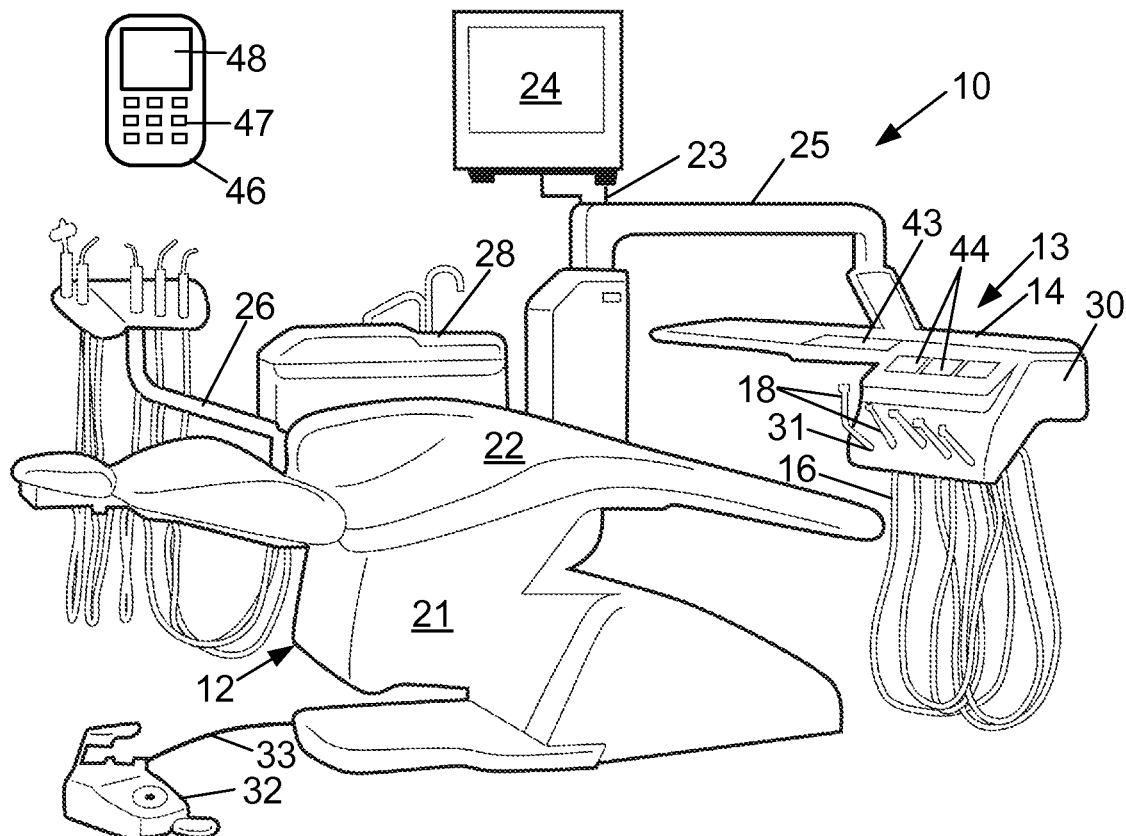
FIG. 2 is a perspective view of the treatment unit of FIG. 1

In this example, as shown in FIG. 2, the patient chair assembly 12 is a dental chair assembly, the user is a dentist, and the handpiece assembly 18 outputs laser energy for a dental procedure. The dental chair assembly 12 includes several components, all supported above the floor by a pedestal 21. The dental chair assembly components include a seat 22 that supports the patient. An instrument section of the apparatus includes a display stand 23 that supports a screen display 24 that is coupled to the PAC device 14, first and second instrument support arms 25 and 26 and a sink 28.

In this example, the PAC device 14 is connected at the end of, and supported by, the first support arm 25. Alternatively, the PAC device 14 may be located within the chair assembly 12, such as beneath the seat 22. The PAC device 14 includes a PAC device housing 30 with multiple pockets 31 for holding multiple handpiece assemblies 18 when they are not in use. The PAC device 14 detects when, and which, handpiece assembly is removed from its pocket, and automatically switches between standby mode (laser disabled) and ready mode (laser enabled) when a handpiece is removed. A footswitch 32 at the bottom of the chair assembly 12 is electrically connected by a footswitch cable 33 to the PAC device 14 to actuate (activate) the handpiece assembly 18 when the treatment unit 13 is in the ready mode.

As shown in FIG. 1, the PAC device 14 in this example includes the following components: A power supply 40 provides electricity to electrically power the handpiece assembly 18. A data storage device 41 includes a hardware storage medium that stores data that is detected or received by the PAC device 14 and software instructions. A processor 42 executes the software instructions for performing the functions of the PAC device 14. An input device 43 may include a keyboard, mouse, touch feature of a touch screen and voice recording and recognition. The input device 43 is used by the dentist to input questions and comments to be uploaded to the assistance center 20 and commands for controlling operation of the treatment unit 13. The input device 43 may further include switches for disabling and enabling activation of the handpiece assembly 18 and for activating the handpiece assembly 18, dials for selecting laser pulse intensity and pulse duration, and valves for manually controlling flow of water and air to the handpiece assembly 18. A display device 44 in this example is integrated into the PAC device 14 and visible through the PAC device housing 30. The display device 44 may include a screen display, indicator lights and gauges for displaying communications received from the assistance center 20 and also operating settings and operating measurements such as a power setting, a pulse duration setting, a measured voltage and current powering the laser module and measured output laser power and a measured laser source temperature.

A remote control interface circuit 45 communicates, either wirelessly or through a cable, with a handheld remote control device 46. The remote control device 46 might be a smartphone or a tablet computer. The remote control device 46 may be used by the dentist to control, through the PAC device 14, operation of the treatment unit 13. Control commands may be entered on an input device 47 of the remote control device 46 by the user pressing keys on a keypad, swiping a mouse pad, touching a touch screen, or applying tilting and jarring movements to the remote control device 46 that are sensed by the remote control device 46. Example commands that can be entered in the remote control device 46 are to set a laser pulse intensity setting and a laser pulse duration setting, or to control release of water or air to the handpiece assembly 18 or release of water or air from the handpiece assembly 18 to the target tissue. A display screen 48 of the remote control device 70 may display operating settings and operating measurements, such as power setting, pulse duration setting, measured voltage and current powering the laser module and measured output laser power and measured laser source temperature.

Figure 3A:
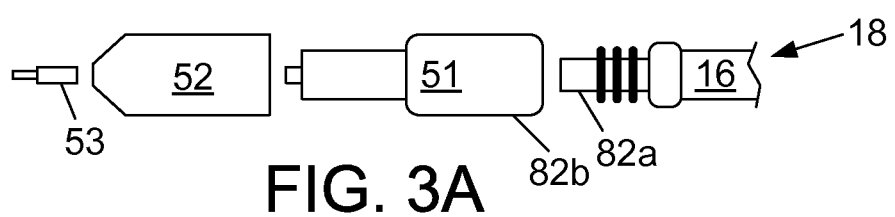
FIG. 3A is an exploded view of the handpiece assembly.
Figure 3B:
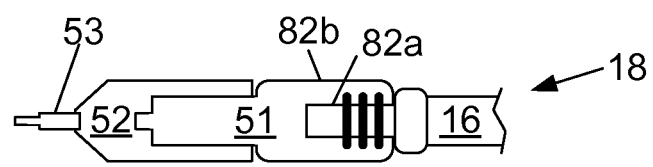
FIG. 3B is an assemble view of the handpiece assembly.

As illustrated in FIGS. 3A and 3B, the handpiece assembly 18 in this example includes a handpiece 51, a laser module 52 and laser tip 53. The dentist is provided with a selection of different handpieces 51, different laser modules 52, different laser tips 53 and different cables 16, to select from to assemble his/her own customized handpiece assembly 18. The dentist inserts the selected cable 16 into the selected laser module 52, and inserts the laser module 52 and the selected tip 53 into the handpiece 51. This enables the dentist to select the cable 16 (e.g., based on length), the handpiece 51 (e.g., to optimize manual manipulation), the laser module 52 (e.g., for best laser wavelength) and the laser tip 53 (e.g., for best laser spot size) that are best suited for the procedure and medical issue (medical condition) at hand.

The handpiece 51 is the part of the handpiece assembly that the dentist grips. The handpieces 51 that the dentist can choose from are application-specification, in that their shape, size and internal configuration are optimized for a particular medical treatment procedure. Example handpieces 51 may include a surgical handpiece, a whitening handpiece and a pain control handpiece. Handpieces may include optical elements (e.g., a lens, mirror, filter, beamsplitter, prism, grating) for processing and directing the laser beam.

The laser module 52 in this example includes a source of laser light, such as a laser diode, a diode-pumped solid state laser, a flash lamp pumped solid state laser, or LED. The laser module 52 includes a water channel to channel water toward, and spray the water on, a target tissue being ablated to both cool the tissue and interact with the laser energy to achieve the ablation. The laser module 52 may be assigned, by its manufacturer, a unique electronic laser module identification (ID) that includes the laser module's serial number, model and calibration parameters. The laser module 52 may include a microprocessor 55 that outputs the ID information when queried and that also controls the operation of laser module 52. A temperature sensor 56 (e.g., thermistor) near the laser source inside the handpiece assembly 18 outputs a temperature signal that indicates a temperature of the laser module 52. The laser module 52 further includes cooling line 57 (FIG. 4) for conducting cooling air around the laser source. The microprocessor may output other feedback data through the cable 16 to the PAC device 14, such as an indication of what laser tip is used. Examples of the laser modules 52 from which the dentist may choose are a 940 nm laser module, a 810 nm laser module, a 660 nm laser module, a blue laser module and a red laser module. The laser module 52 has an aiming-light aperture 58 (FIG. 4) that projects visible aiming light onto the target tissue to assist the user in aiming the laser pulse by indicating where the laser pulse will strike on the target tissue. The laser module 52 further has an LED ready light 59 (FIG. 4), which is powered by a laser-ready signal when the laser source may be activated.

The laser tips 53 may include optical elements, (e.g., a lens, mirror, filter, beamsplitter, prism, grating) with different focal lengths.

Figure 4:
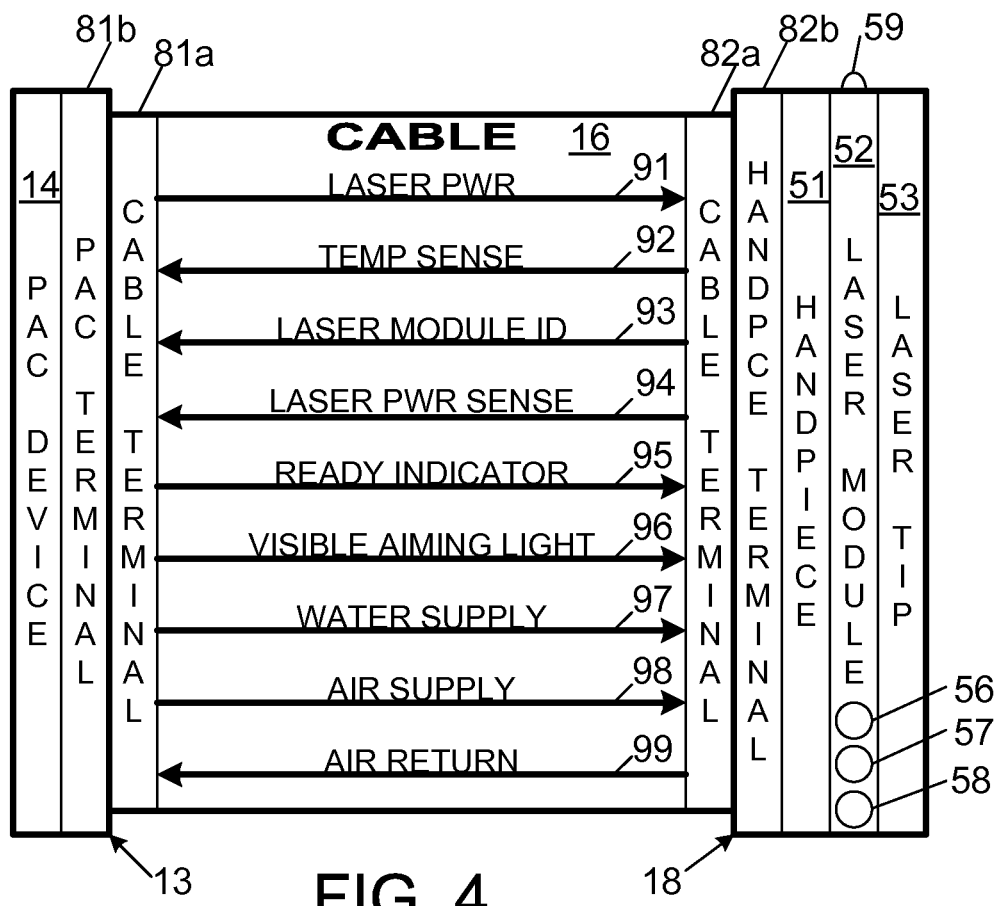
FIG. 4 is a schematic diagram of the cable.

As illustrated in FIG. 4, the cable (hose) 16 has first and second electrical plug terminals 81a, 82a at its opposite ends, that are removably attachable respectively to a corresponding electrical socket terminal 81*b* of the PAC device 14 and a corresponding electrical socket terminal 82*b* of the laser module 52 of the handpiece assembly 18. The terminal 81*b* of the PAC device 14 may be on the PAC device housing 30 or may be on a housing of the chair assembly 12. Since different chair assemblies may have different terminals, the first hose terminal 81*a* may be specifically configured to match the terminal of that brand of chair assembly 12.

The cable 16 in this example has a laser power line 91 that conducts electrical supply current from the PAC device 14 to the handpiece assembly 18 to power the laser module 52. The cable 16 further may have the following electric signal lines that conduct data between the PAC device 14 and the handpiece assembly 18: Lines for conducting data from the handpiece assembly to the PAC device 14 include a temperature sensor line 92 for communicating the temperature sensor output of the temperature sensor 56, a laser ID line 93 for communicating the laser module ID information, and a laser output power sense line 94 for communicating the laser output power sensor (photodiode) output. A system-ready line 95 conducts a system-ready signal from the PAC device 14 to the handpiece assembly 18, to power the system-ready light 59. An optical fiber 96 conducts the visible aiming light to the handpiece assembly 18 for the aiming light aperture 58. A water supply line 97 conducts water to the handpiece assembly 18. An air supply line 98 and an air return line 99 conduct cooling air respectively from the PAC device 14 to the handpiece assembly and from the handpiece assembly back to the PAC device 14.

As shown in FIG. 1, the PAC device 14 further includes an assistance-center communication circuit 100, to provide a communication link (portrayed with double-headed arrows in FIG. 1) with the user assistance center 20 through a network 102, such as the Internet. The user assistance center 20 may be housed in a facility (e.g., building or room in a building) that is remote from (e.g., in a different building, city or country from) the system. The assistance center 20 may include a hardware server 110 for uploading the data from the PAC device 14 and downloading the program updates and control instructions and the user information to the PAC device 14. The server 110 includes a data storage device 111, comprising a hardware storage medium that stores software instructions, and a processor 112 (which may comprise one or more individual processors) that executes the instructions for performing the functions of the server 110. The server's data storage device 111 also stores data to be downloaded to the PAC device 14 and data that was uploaded from the PAC device 14. The assistance center 20 may include personnel for controlling operation of the server 110, which includes controlling what data and information the server 110 downloads and how the server 110 processes the information it uploads. The personnel may include customer service experts for operating, troubleshooting and repairing the medical units 13. The assistance center 20 may be owned by, operated by, and part of, the manufacturer or distributor of the treatment units 13.

The PAC device 14 may monitor, and upload to the user assistance center 20, data relating to operation of the handpiece assembly 18 during medical procedures. The monitored operational data may include data the PAC device 14 receives from the handpiece assembly 18, such as measured laser source temperature, measured laser output power, laser module 52 used and laser tip 18 used. The operational data may further include settings implemented by the PAC device 14, such as power setting used and pulse duration setting used. The operational data may yet further include data detected and measured by the PAC device 14, such as measured current and voltage output to the handpiece assembly, and an identification of the cable or other attachment used. The data may yet further include operational notes that are input by the dentist into the input devices 43, 47, such as attachments used and selections made. The PAC device 14 may upload the data in real time, or in the form of a time log, noting what the medical unit 13 did and what the settings and measured values were and which attachments were used, and including when the laser source was activated and the duration of the activation. The designation of attachments may include which cable 16, handpiece 51, laser module 52, and laser tip 53 were used.

The uploaded data may further include questions and comments entered by the dentist into the input devices 43, 47. The questions and comments may be regarding a medical procedure being performed or a non-medical issue (e.g., product warrantee) relating to the unit 13 or regarding general information unrelated to a current issue. For example, a question might include the medical condition being treated and a request for advice on what procedure to use and what attachments and settings to use. Another question might be in general about which attachments are best for which procedures. Another question might be about the medical unit's warrantee or about a malfunction or problem in using the medical unit 13. A comment might include the dentist's notes regarding the medical condition currently treated and the treatment procedure being used (including what settings and attachments used), and what the procedure's results to the patient are. Another comment might include advice on use of the medical unit 13 based on the present dentist's personal experience, which other unit users would find educational. Each question and comment may be designated by the dentist to be directed to either the assistance center's personnel and/or for dissemination to other dentists using the units. In one example, a question from a first dentist might be disseminated by the assistance center 20 to other dentists using the unit, and comments from the other dentists might be in response to the first dentist's question. Downloaded information (e.g., answers and comments from other dentists) may be displayed to the dentist by any of the displays 24, 44, 48.

Figure 5:
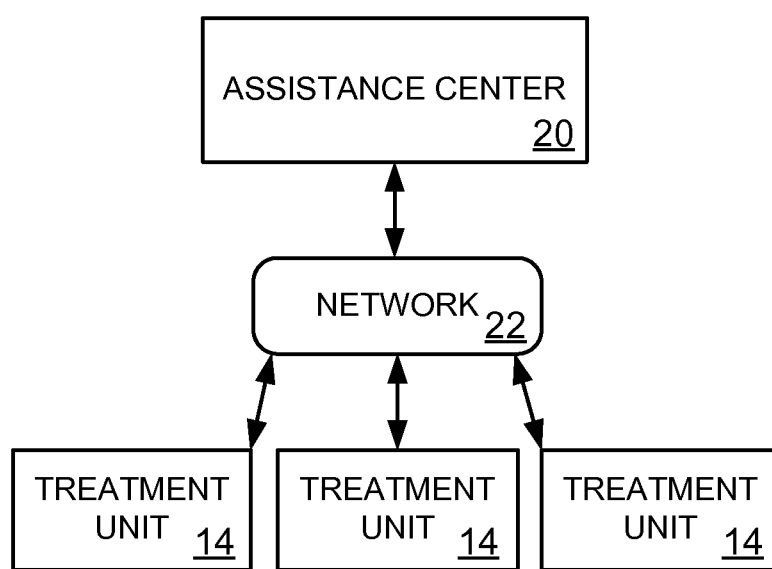
FIG. 5 is a schematic diagram showing communication paths between the user assistance enter and multiple treatment units like the treatment unit of FIG. 1.

As shown in FIG. 5, there may be many medical treatment units 13 like the unit 13 shown in FIG. 1, located remote from each other and from the assistance center 20, such as in different buildings or cities or countries, and used by different dentists. The assistance center 20 may continuously monitor the data being uploaded by the medical units 13, store the data on the server's data storage device 111, plot the data, mathematically (including statistically) process the data, analyze the data and prepare reports that include a summary and analysis of the data.

Results of the data analysis may be used by the assistance center 20 to update the software that controls the PAC device 14. The updated software may then be downloaded to the PAC devices 14 of the medical units 13 to improve operation of the medical units 13. The software improvement may be based on (1) input (e.g., questions, recommendations and reports of problems) uploaded from the dentists and (2) operational parameters detected (including measured) by the medical units 13 independent of dentists' knowledge or input. The resulting software updates, based on uploaded data from some or all of the medical units 13, may be downloaded to all of the medical units 13. Each unit 13 implements the update by revising its operating software in accordance with the update revision, or by replacing its operating software with the update revision.

Some examples of what software update revisions are based on are as follows:

The software update may improve on a feature based on what the manufacturer has found to be desirable through its internal experimentation or quality control assessments. For example, the software update may correct a software glitch found by the manufacturer's own quality control tests or eliminate a high laser power option that the quality control tests find leads to shortened laser source life.

The software update may add an operational feature that users recommend. For example, if dentists' comments recommend adding a particular pulse duration option to an offered list of pulse duration options, that particular requested pulse duration option may be added in the next software update that is downloaded to all medical units 13.

The software update may add operational features based on operating data detected (including measured) by the PAC devices 14. For example, if the uploaded operating data indicate that dentists are often using the very lowest pulse duration option, then the assistance center 20 may deduce that dentists would use an even lower pulse duration option if it were available, and the assistance center 20 may make that even-lower pulse duration option available in the next software update.

The software update may prune operational options that are not being used or problematic. For example, if the uploaded operating parameter data indicate that a particular pulse duration option is not being used, the next software update may delete that pulse duration option from a list of pulse duration options. The next software update may also delete a pulse duration option that is found to be problematic based on dentists' uploaded questions and comments and/or based on parameters detected and uploaded (even without dentists' interaction or knowledge) by the PAC device 14.

A software update may adjust a feature in a way that depends on the operating condition. For example, if the uploaded data indicates that a particular pulse intensity tends to cause laser overheating only in a particular model of laser module 52, then the next software update may eliminate that particular pulse intensity option from a pulse intensity option list only when the PAC device 14 detects that particular laser model 52 is connected to the cable 16. As another example, the uploaded data might indicate dentists are using a first range of pulse intensities when using a first model of laser module and using a second, different, range of pulse intensities when using a second model of laser module. In that case, the software update might list optional pulse intensities that are only in the first range when (as detected by the PAC device 14) the first laser model is used and that are only in the second range when the second laser model is used.

The uploaded data may provide reliability information about how the treatment devices' components are performing in the field. This would augment the manufacturer's own internally-generated quality assurance (QA) reliability test results. For example, the uploaded data, which includes both laser input power and laser output power, may indicate a gradual degradation in laser efficiency (output power per input power) for a particular laser module model. If the uploaded data is from many (for example in the hundreds) medical units 13, the precision of any statistical assessment derived from this uploaded data would surpass the precision of any statistical assessment derived from the manufacturer's QA lab. A product reliability assessment derived from the uploaded data would also be more relevant to what to expect from field use of the unit 13 than product reliability results derived from the manufacturer's QA lab.

The uploaded data may enable the manufacturer to predict product failure and prevent it from occurring. For example, if the uploaded data indicates a gradual degradation in efficiency by a laser module of a particular model or production batch, the manufacturer may issue a product recall of all laser modules of that model or production batch. The product recall may precede, and thus prevent, any laser modules of that model actually failing in the field. Also, being informed of the degradation before a product failure actually occurs gives the manufacturer more time to prepare for the recall (such as by ramping up production of replacement laser modules), as opposed to if the first indication of a problem were a report of products already failing.

The uploaded data may also enable the manufacturer to determine whether or not a unit's degradation is due to a system-wide problem with all units of particular model or production patch, or only an isolated incident. For example, if uploaded data from one unit 13 in one dentist office indicates a particular component is degrading while uploaded data from other units 13 in other dentist offices indicate components of the same model and production batch are not degrading, the manufacturer may deduce that the problem is unique to that particular component and not a systemic problem with that component's model or batch. This would enable the manufacturer to send a replacement component to the dentist, before the component fails and without a product recall.

The uploaded data may also be used to verify an assertion by dentists about his/her unit's performance. For example, if a dentist asserts that the unit performed improperly on a particular date under a particular set of conditions, the uploaded data will indicate the accuracy of the dentist's assertion. And because the dentist is aware of the uploaded data being available to the manufacturer, the dentist will be more inclined to ensure that his/her assertion is accurate.

The uploaded data, combined with the downloaded control instructions, facilitates remote diagnostic troubleshooting. For example, if the dentist reports a problem with the unit 13, downloaded control instructions may control the unit to perform different diagnostic test procedures including operating in different modes, and the uploaded data would indicate how the unit responded. For example, the control instructions may control the power supply to drive the laser module at different power levels, and the uploaded data may indicate, for each power level, a measured power that is input by the laser module and a measured power that is output by the laser module. A customer service expert at the assistance center 20 may then use this data to troubleshoot the unit 13, all without assistance by the dentist.

Statistical analysis of the uploaded data over time may be used by the manufacturer to recognize changes in trends, over time, in how the unit is being used. Knowledge of how the trends are changing enables the manufacturer to anticipate market demand for each of the unit's attachments and optimize the unit's design. For example, if the uploaded data indicates that, of all laser module models dentists have in their offices, use of a first model is increasing over the course of several months while use of a second model is decreasing over those same months, the manufacturer might anticipate an increase in future sales of the first model and a decrease in future sales of the second model. The manufacturer may also determine what aspect of the second model makes it increasingly used and optimize that aspect in future models.

Statistical analysis of the uploaded data, received from many or all of the units 13, may yield reports on trends in how dentists are using the system. These reports may be downloaded to one or more of the units 13, to be displayed to one or more of the dentists on any of the dentists' displays 24, 44, 48. For example, the reports may summarize, for each type of treatment for each type of medical condition, what selections dentists (who use the units 13) are making in terms which attachment (e.g., cable, handpiece, laser module, laser tip) and operating parameter (e.g., pulse intensity and duration), and what the medical outcomes (derived from the dentists' uploaded comments) are as a function of what selections are made. The results may be categorized by geographic area and by level of dentist experience and by dentist ranking in patient satisfaction surveys. The results may be part of the downloaded information to be displayed by the PAC device 14 to the dentist. The results may also be used by a customer service expert at the assistance center 20 to advise the dentist on the most commonly used attachment selections and setting selections for performing a particular medical procedure for a particular medical issue.

Statistical analysis of a particular dentist's uploaded data may result in a personalized report particularly relating to the particular dentist's use of the system and derived primarily or solely from uploaded data from the dentist's own unit 13. The personalized report may be downloaded to the particular dentist's unit 13, and may include summaries and graphs and tabulations of the dentist's uploaded data, and results of statistical analysis of the data.

The arrangement described above provides interchange of information between dentists, including sharing of experiences. This may foster a camaraderie between users of the medical units, and also between each unit user and the manufacturer. It also helps educate a user on best practices for using the unit. It also gives the user a feeling that he/he is not alone in the use of the unit 13. The downloaded information may include on-line education, training and special events to the PAC device 14 for display on any of the unit's displays 24, 44, 48.

The arrangement described above, based on two-way communication between the PAC device 14 and the assistance center 20, may be subscribed to by a dentist and may be implemented in accordance with subscription or licensing business arrangement between the dentist and a party associated with the assistance center 20. The party with whom the dentist subscribes might be a manufacturer or distributer (vendor) of the unit 13. The dentist may be billed for the subscription as a monthly fee or a one-time fixed price. The subscription may entitle the dentist to an extension on the laser modules' warrantee, such as a lifetime free laser module exchange agreement. The subscription makes the extended warrantee and exchange agreement more financially feasible to the manufacturer, by giving the manufacturer an ability to monitor usage of the laser module 52 and thus to verify that the laser module 52 was used properly.

The server 110 may store the uploaded data (including data detected by the units 13 themselves, and questions and comments from dentists) on the storage device 111 for long term storage, to make the data available for future applications that are not envisaged when the data is being collected. One such application includes data mining, in which a large amount of data is analyzed to discover patterns and relationships. This can include future direct marketing and target marketing for a future new product. For example, if the manufacturer develops and starts marketing a new model of laser module, the manufacturer may analyze the stored data to determine which dentists are likely to want the new model and which dentists are not. The manufacturer may then send email advertisements to the target group of dentists who will appreciate the new product and not to the dentists who will consider emailed advertisements for this product as annoying junk mail.

Figure 6:
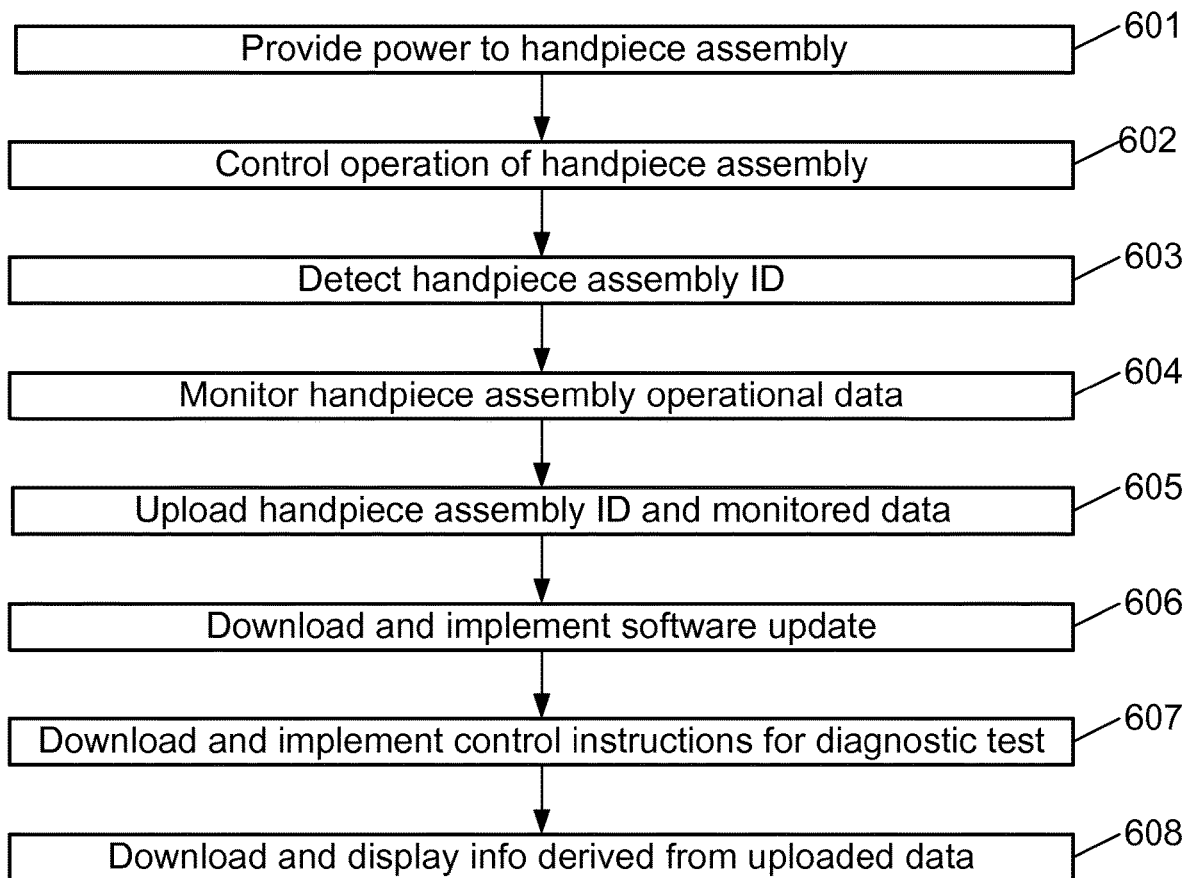
FIG. 6 is a flow chart of steps performed by PAC device.

FIG. 6 is a flow chart of steps performed by the PAC device 14. The PAC device provides electrical power through a cable to a laser handpiece assembly to electrically power a laser source within the handpiece assembly (step 601). The PAC device controls operation of the handpiece assembly (602), detects an identification of the handpiece assembly (603), and monitors data relating to operation of the handpiece assembly (604). The PAC device uploads, to the assistance center, the handpiece assembly identification and the monitored data (605). The PAC device downloads and implements a software update (606) that is derived from the uploaded data. The PAC device also downloads and implements control instructions to perform a diagnostic test, and uploads resulting data to the assistance center (607). The PAC device also downloads information that is derived from the uploaded data, and displays the information to a user (608).

Figure 7:
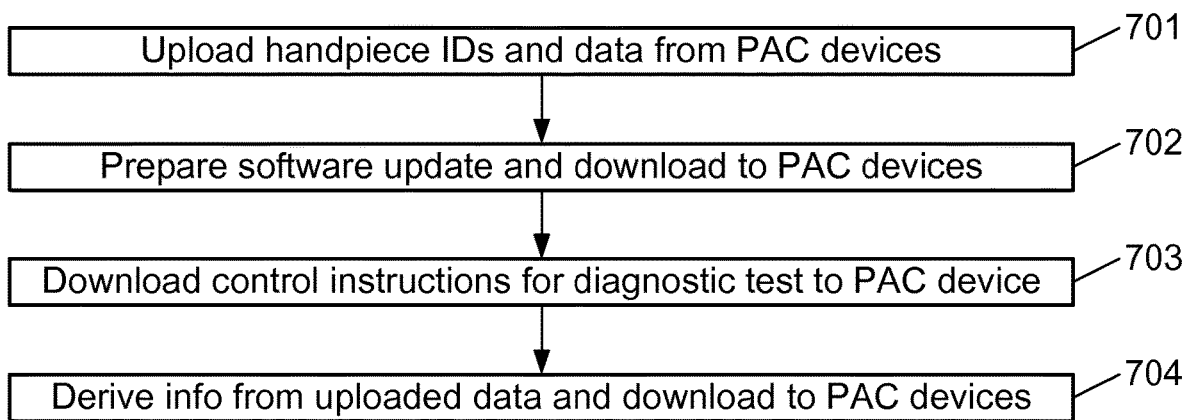
FIG. 7 is a flow chart of steps performed by a server of the assistance center.

FIG. 7 is a flow chart of steps performed by the server 110. The server uploads, from each PAC device 14, through the network 22, the respective handpiece assembly identification and the monitored data (step 701). The server prepares a software update based on the uploaded data, and downloads the update to the PAC devices (702). The server downloads, to each PAC device, control instructions that control the PAC device to perform a diagnostic test and upload resulting data to the assistance center (703), and receives the uploaded resulting data from the respective PAC device. The server derives information from the uploaded data, and downloads the information to the PAC devices to be displayed by the PAC devices (704).

The components and procedures described above provide examples of elements recited in the claims. They also provide examples of how a person of ordinary skill in the art can make and use the claimed invention. They are described here to provide enablement and best mode without imposing limitations that are not recited in the claims.

The invention claimed is:

1. A system for providing a user assistance center and a remotely located dental treatment power and control (PAC) device, comprising:
   a user assistance center configured to receive at least one input into the dental treatment PAC device regarding use of the dental treatment PAC device; and
   the dental treatment PAC device configured to:
   provide electrical power to a handpiece assembly;
   control operation of the handpiece assembly;
   detect an identification of the handpiece assembly upon selection, by the user, of the handpiece assembly from among a plurality of handpieces;
   automatically switch a laser source of the handpiece assembly to ready mode based on the identification without further action from the user;
   monitor data relating to operation of the handpiece assembly; and
   upload, through the communication network to the user assistance center that is remote from the dental treatment PAC device, the handpiece assembly identification and at least a portion of the monitored data.

2. The system of claim 1 wherein the PAC device is further configured to: download, through the network from the assistance center, control instructions that control operation of the PAC device to perform a diagnostic test and upload resulting data to the assistance center; and implement the control instructions.

3. The system of claim 1, wherein the PAC device is further configured to download, through the communication network from the user assistance center, information that is derived from the uploaded data, and display the information to a user of the system.

4. The system of claim 2, wherein the information includes a statistical analysis of the uploaded data.

5. The system of claim 1, wherein the uploaded data includes a time log of operation of the laser source.

6. The system of claim 1, wherein the uploaded data includes a measurement of a temperature in the handpiece assembly and a measurement of laser power that is output by the handpiece assembly.

7. The system of claim 1, wherein the updated data includes notes entered by the user identifying a medical condition being treated, a treatment procedure the user is using, and the procedure's results to the patient.

8. The system of claim 1, wherein the PAC device is further configured to receive, from the user, a question regarding a medical procedure being performed using the system; upload the question to the assistance center through the network to the assistance center; download an answer to the question though the network from the assistance center; and display the answer to the user.

9. The system of claim 1, further comprising a dental patient chair assembly that is configured for seating a dental patient undergoing treatment by the handpiece assembly and that supports the PAC device.

* * * * *